United States Patent [19]

Huizer et al.

[11] 4,188,497

[45] Feb. 12, 1980

[54] PURIFICATION OF 3,5-XYLENOL

[75] Inventors: Leendert Huizer; Dirk J. Van Namen; Pieter J. D. Oranje, all of Amsterdam, Netherlands

[73] Assignee: Shell Oil Company, Houston, Tex.

[21] Appl. No.: 872,132

[22] Filed: Jan. 25, 1978

[30] Foreign Application Priority Data

Feb. 2, 1977 [GB] United Kingdom ............... 4201/77

[51] Int. Cl.$^2$ ..................... C07C 37/06; C07C 37/22
[52] U.S. Cl. .................................. 568/799; 568/749
[58] Field of Search ............... 568/756, 749, 772, 799

[56] References Cited

U.S. PATENT DOCUMENTS

| | | | |
|---|---|---|---|
| 2,156,402 | 5/1939 | Prahl | 568/749 |
| 2,413,598 | 12/1946 | Ballard et al. | 568/799 |
| 3,351,669 | 11/1967 | Anderson et al. | 586/756 |
| 3,829,509 | 8/1974 | Charles et al. | 568/799 |
| 3,859,365 | 1/1975 | Young | 568/799 |
| 4,086,282 | 4/1978 | Wattimena | 568/799 |

OTHER PUBLICATIONS

"Smith College Chemistry", Sixth ed. (1946) by Ehret, pp. 555, 638, 639 and 644.

*Primary Examiner*—Werren B. Lone

[57] ABSTRACT

A process is described for the removal of halogen residues from a reaction mixture containing 3,5-xylenol and halogen residues, produced via the heating of isophorone at a temperature of about 450° C. to about 650° C. in the presence of a homogeneous halogen-containing catalyst, said removal being accomplished by contacting the reaction mixture with a metal selected from the group consisting of zinc, iron, magnesium, cadmium, cobalt and nickel.

4 Claims, No Drawings

PURIFICATION OF 3,5-XYLENOL

BACKGROUND OF THE INVENTION

It is known, according to copending application, Ser. No. 681,358, filed Apr. 29, 1976 now U.S. Pat. No. 4,086,282, that 3,5-xylenol is advantageously prepared by a process which comprises heating isophorone at a temperature of from about 450° C. to about 650° C. in the presence of a homogeneous catalyst comprising a halogen having an atomic number of at least 17 or an organic compound containing such halogen. However, it has been found that this process results in a product xylenol which is contaminated by a residue of free halogen and multiple organic halide compounds. The variety and the chemical nature of such halogen residue compounds do not permit their effective separation from the xylenol product by conventional means such as fractional distillation.

The utility of 3,5-xylenol as a solvent, a disinfectant, an oxidation inhibitor, and an intermediate in chemical synthesis and its use in processes for ore flotation and for production of resins and plastics are well recognized. Many of these potential applications for the 3,5-xylenol produced, as described above, by methods involving a homogeneous halogen catalyst would be precluded unless the halogen residues could be efficiently and effectively removed from the 3,5-xylenol product. Furthermore, it has been found that unless the halogen residues are substantially removed from the product xylenol, the mixture is corrosive to mild steel, thus creating problems in the processing, transport, and storage of the xylenol. For instance, the presence of significant quantities of halogen residues in the reaction product mixture requires that distillation columns for separation of unreacted isophorone and reaction byproducts from the crude 3,5-xylenol must be constructed of expensive corrosion-resistant alloy materials. Therefore, it would be of advantage if a process was available whereby halogen residues could be efficiently and effectively removed from the xylenol product.

SUMMARY OF THE INVENTION

It has now been found that halogen residues can be removed from a reaction mixture containing 3,5-xylenol and halogen residues, which has been produced by the heating of isophorone to a temperature of 450° C. to 650° C. in the presence of a homogeneous catalyst comprising a halogen having an atomic number of at least 17 or an organic compound containing such a halogen, said removal being accomplished by contacting the reaction mixture with at least one metal chosen from the group consisting of zinc, iron, magnesium, cadmium, cobalt, and nickel. Removal of halogen residues by means of this process yields a xylenol product essentially devoid of halogen in either free or combined form.

DESCRIPTION OF THE PREFERRED EMBODIMENTS

The metal employed in the process according to this invention is preferably in a divided form, most preferably in finely divided or powdered form. The amount of metal used is generally from about 0.01% to about 5% by weight (%w), based on the weight of 3,5-xylenol. The optimum amount of metal used in a particular application will be dependent upon the amount of halogen added as catalyst to the reaction for the preparation of 3,5-xylenol from isophorone. Generally, addition of metal in the range of 0.1 to 1%w, based on the weight of 3,5-xylenol, will be sufficient. The preferred metals are zinc, iron, and magnesium, with zinc being most preferred.

The process of the invention may be conveniently carried out by heating the crude 3,5-xylenol reaction mixture containing the halogen residues with the metal at a temperature of about 100° to about 200° C. for a period of approximately 0.5 to 5 hours. The process may be suitably employed in a continuous or batch manner, and may suitably involve contact of the reaction mixture with one or more of the group of metals in one or more stages. Following contact of the crude reaction mixture with the metal, the 3,5-xylenol product may be separated from a mixture also comprising halogen-loaded metal and unreacted isophorone and byproducts of the isophorone to xylenol reaction in one or more separation zones. For instance, a vacuum distillation procedure may be used to distill from the mixture purified 3,5-xylenol as an overhead product. However, for commercial scale operation it is advantageous to first remove unreacted metal and halogen-loaded metal from the mixture in one or more liquid/solid separation zones, employing such conventional techniques as gravity settling, filtration, centrifugation, etc. Further processing to purify the desired 3,5-xylenol by removal of unreacted isophorone and byproducts of the isophorone to xylenol reaction is then accomplished in one or more distillation zones. Isophorone may be optionally separated from the byproducts and recycled as feedstock for further xylenol production.

It has been found that the removal of halogen residues from the crude reaction mixture is responsible for significant decreases in the corrosivity of the mixture in both the gas and liquid phases to mild steel and the lower alloy steels. By means of this invention it is feasible to utilize less expensive metallurgy in the downstream processing of the crude xylenol reaction mixture. For instance, distillation columns and associated equipment for separation of 3,5-xylenol and isophorone from the mixture may be constructed of less corrosion resistant materials than was heretofore possible.

The invention is illustrated further in the following Examples.

EXAMPLES 1 to 3

3,5-Xylenol was prepared by heating isophorone at 600° C. in the presence of 1.0%w methyl iodide, based on the weight of isophorone, according to procedures described in the copending application referenced above. The crude phenol thereby produced contained 0.5% by weight of iodine in free and combined form.

The metals used in Examples 1 to 3 were as follows:
Example 1, powdered zinc (Billiton 110, average particle size 3 micron);
Example 2, magnesium turnings (March, 99.5% pure);
Example 3, powdered iron (Brocacef B.V., Maarsen).

The crude 3,5-xylenol reaction mixture comprising halogen residues containing 0.5% w iodine and the metal (0.2%w based on 3,5-xylenol) were heated together for one hour at 180° C. under atmospheric pressure. The 3,5-xylenol was then distilled off under a pressure of 10 mm Hg and the iodine content of the purified xylenol product was determined. The results are given in the following Table I.

TABLE I

| Example | Metal | Iodine content of the purified 3,5-xylenol (ppm) |
|---|---|---|
| 1 | Zn | 18 |
| 2 | Mg | 87 |
| 3 | Fe | 30 |

EXAMPLE 4

The corrosivity of the purified 3,5-xylenol from Example 1 was determined by heating the product with a plate of mild steel in an autoclave at 250° C. for 7 days and measuring the amount of metal removed. The corrosivity expressed in millimeters (mm) of metal removed per year was obtained for both the liquid and gaseous product and compared with data similarly obtained for the crude 3,5-xylenol. The results are given in Table II below.

TABLE II

| 3,5-xylenol | Corrosivity (mm/year) | |
|---|---|---|
|  | gas-phase | liquid-phase |
| purified | 0.01 | 2.7 |
| crude | 0.6 | 14.0 |

What is claimed is:

1. In the process in which isophorone is heated to a temperature of about 450° C. to about 650° C. in the presence of a homogeneous catalyst comprising a halogen having an atomic number of at least 17 or an organic compound containing said halogen to produce a liquid reaction mixture containing 3,5-xylenol and halogen residues from which reaction mixture the halogen residues are subsequently removed, the improvement which comprises contacting, at a temperature of from about 100° to about 200° C. for a period of approximately 0.5 to 5 hours, the reaction mixture with at least one metal selected from the group consisting of zinc, iron, magnesium, cadmium, cobalt, and nickel, using from about 0.01% to about 5% by weight of the metal, based on the weight of 3,5-xylenol in the reaction mixture, thereby removing halogen residues from the reaction mixture.

2. The process of claim 1, wherein the metal is selected from the group consisting of zinc, iron, or magnesium.

3. The process of claim 2, wherein the metal is in finely divided or powdered form.

4. In the process in which isophorone is heated to a temperature of about 450° C. to about 650° C. in the presence of a homogeneous catalyst comprising a halogen having an atomic number of at least 17 or an organic compound containing said halogen to produce a crude reaction mixture comprising 3,5-xylenol, halogen residues, isophorone, and organic by-products from which a purified 3,5-xylenol product is subsequently recovered, the improvement which comprises recovering the 3,5-xylenol product by:
   a. contacting, at a temperature of from about 100° C. to about 200° C. for a period of approximately 0.5 to 5 hours, the crude reaction mixture in a reaction zone with at least one metal selected from the group consisting of zinc, iron, magnesium, cadmium, cobalt, and nickel, using from about 0.01% to about 5% by weight of the metal, based on the weight of 3,5-xylenol in the reaction mixture, thereby producing a mixture of a solid phase containing halogen-loaded metal and a liquid phase essentially free of halogen residues;
   b. separating the mixture produced in step (a) in one or more liquid/solid separation zones to remove the solid phase from the liquid phase; and
   c. separating in one or more distillation zones purified 3,5-xylenol from the liquid phase.

* * * * *